(12) United States Patent
Locke et al.

(10) Patent No.: US 9,962,254 B2
(45) Date of Patent: May 8, 2018

(54) ABSORBENT SUBSTRATES FOR HARVESTING SKIN GRAFTS

(71) Applicant: KCI Licensing, Inc., San Antonio, TX (US)

(72) Inventors: Christopher Brian Locke, Bournemouth (GB); Timothy Mark Robinson, Basingstoke (GB); John R. Harper, Boerne, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days. days.

(21) Appl. No.: 14/211,026

(22) Filed: Mar. 14, 2014

(65) Prior Publication Data

US 2014/0277454 A1   Sep. 18, 2014

Related U.S. Application Data

(60) Provisional application No. 61/860,822, filed on Jul. 31, 2013, provisional application No. 61/782,385, filed on Mar. 14, 2013.

(51) Int. Cl.
*A61F 2/10* (2006.01)
*A61F 2/00* (2006.01)
(Continued)

(52) U.S. Cl.
CPC .......... *A61F 2/105* (2013.01); *A61B 17/322* (2013.01); *A61F 2/0095* (2013.01);
(Continued)

(58) Field of Classification Search
CPC ........ A61L 15/42; A61L 15/425; A61L 15/26; A61L 15/58; A61L 317/322;
(Continued)

(56) References Cited

U.S. PATENT DOCUMENTS 2,379,574 A   7/1945   Goldthwait
2,579,039 A   12/1951  Evans
(Continued)

FOREIGN PATENT DOCUMENTS

CN   2125374 U   12/1992
CN   2596950 Y   1/2004
(Continued)

OTHER PUBLICATIONS

BBC_Gore-Tex (http://www.bbc.co.uk/schools/gcsebitesize/science/ocr_gateway_pre_2011/carbon_chem/6_designer_polymers3.shtml.) Accessed Apr. 22, 2015.*

(Continued)

*Primary Examiner* — Christopher D Prone
*Assistant Examiner* — Rokhaya Diop
(74) *Attorney, Agent, or Firm* — Reza Mollaaghababa; Thomas J. Engellenner; Pepper Hamilton LLP (57) ABSTRACT

Methods and devices for management of fluids during skin graft transplantation are disclosed. In one aspect of the invention, absorbent substrates for transplanting skin grafts are disclosed having a surface adapted to contact at least one excised skin graft and engage said graft for removal from a donor site; a sealing member at least partially surrounding an absorbent material disposed within the enclosure; wherein at least a portion of the skin-contacting surface is porous and in fluid communication with the absorbent layer to capture fluids.

44 Claims, 6 Drawing Sheets

(51) Int. Cl.
  *A61B 17/322* (2006.01)
  *A61F 13/00* (2006.01)
  *A61F 13/02* (2006.01)
(52) U.S. Cl.
  CPC ...... *A61F 13/00051* (2013.01); *A61F 13/025* (2013.01); *A61F 13/0206* (2013.01); *A61F 13/0213* (2013.01); *A61F 13/0223* (2013.01); *A61F 13/0226* (2013.01); *A61F 13/0259* (2013.01); *A61B 2017/3225* (2013.01)
(58) Field of Classification Search
  CPC .... A61L 2017/3225; A61F 2/10; A61F 2/105; A61F 13/00029; A61F 13/00072; A61F 13/00076; A61F 13/0008; A61F 13/00085; A61F 2013/00089; A61F 2013/00106; A61F 2013/00323; A61F 2013/00327; A61F 2013/00268; A61F 2013/00157; A61F 13/0206; A61F 13/0223; A61F 13/0213; A61F 13/0259; A61F 13/025; A61F 13/00051; A61F 2/0095; A61F 13/0226; A61F 2017/3225; A61B 17/322; A61B 2017/3225
  See application file for complete search history.

(56) References Cited

U.S. PATENT DOCUMENTS

| | | | |
|---|---|---|---|
| 2,721,555 A | 10/1955 | Jenny | |
| 3,054,404 A | 9/1962 | Meek | |
| 3,782,387 A | 1/1974 | Falabella | |
| 4,345,374 A | 8/1982 | Jacobson | |
| 4,600,533 A * | 7/1986 | Chu | 530/356 |
| 4,605,010 A | 8/1986 | McEwen et al. | |
| 4,666,447 A | 5/1987 | Smith | |
| 4,679,324 A | 7/1987 | Krik | |
| 4,773,418 A | 9/1988 | Hettich | |
| 4,917,086 A | 4/1990 | Feltovich et al. | |
| 5,015,584 A | 5/1991 | Brysk | |
| 5,163,955 A | 11/1992 | Love et al. | |
| 5,386,633 A | 2/1995 | Kanno | |
| 5,433,221 A | 7/1995 | Adair | |
| 5,441,490 A | 8/1995 | Svedman | |
| 5,460,939 A | 10/1995 | Hansbrough | |
| 5,476,478 A | 12/1995 | Jackson | |
| 5,489,304 A | 2/1996 | Orgill | |
| 5,496,339 A | 3/1996 | Koepnick | |
| 5,545,222 A | 8/1996 | Bonutti | |
| 5,571,098 A | 11/1996 | Domankevitz | |
| 5,595,570 A | 1/1997 | Smith | |
| 5,686,303 A | 11/1997 | Korman | |
| 5,730,717 A | 3/1998 | Gelbfish | |
| 5,759,193 A | 6/1998 | Burbank | |
| 5,792,173 A | 8/1998 | Breen et al. | |
| 5,817,115 A | 10/1998 | Nigam | |
| 5,888,219 A | 3/1999 | Bonutti | |
| 5,914,261 A | 6/1999 | Boulton et al. | |
| 5,914,264 A | 6/1999 | Korman | |
| 5,921,980 A | 7/1999 | Kiru | |
| 5,972,476 A | 10/1999 | Field | |
| 5,976,163 A | 11/1999 | Nigam | |
| 6,056,738 A | 5/2000 | Marchitto | |
| 6,063,094 A | 5/2000 | Rosenberg | |
| 6,071,247 A | 6/2000 | Kennedy | |
| 6,071,267 A | 6/2000 | Zamierowski et al. | |
| 6,080,166 A | 6/2000 | McEwen et al. | |
| 6,083,236 A | 7/2000 | Feingold | |
| 6,248,114 B1 | 6/2001 | Ysebaert | |
| 6,254,580 B1 | 7/2001 | Svedman | |
| 6,358,260 B1 | 3/2002 | Ross | |
| 6,364,908 B1 | 4/2002 | Ysebaert | |
| 6,402,770 B1 | 6/2002 | Jessen | |
| 6,436,078 B1 | 8/2002 | Svedman et al. | |
| 6,585,939 B1 | 7/2003 | Dapprich | |
| 6,612,310 B2 | 9/2003 | Sklar | |
| 6,623,498 B1 | 9/2003 | Ziemer | |
| 6,693,077 B1 | 2/2004 | Ruben et al. | |
| 6,800,282 B1 | 10/2004 | Thomson | |
| 6,860,904 B2 | 3/2005 | Bonutti | |
| 7,056,327 B2 | 6/2006 | Levesque et al. | |
| 7,078,582 B2 | 7/2006 | Stebbings | |
| 7,137,979 B2 | 11/2006 | Conrad et al. | |
| 7,207,998 B2 | 4/2007 | Feingold | |
| 7,208,006 B2 | 4/2007 | Fleischman | |
| 7,244,444 B2 | 7/2007 | Bates | |
| 7,513,902 B2 | 4/2009 | Banbury et al. | |
| 7,540,875 B2 | 6/2009 | Jessen | |
| 7,625,384 B2 | 12/2009 | Eriksson | |
| 7,651,507 B2 | 1/2010 | Mishra | |
| 7,666,134 B2 | 2/2010 | Eriksson | |
| 7,666,192 B2 | 2/2010 | Seegert | |
| 7,708,746 B2 | 5/2010 | Eriksson | |
| 7,727,760 B2 | 6/2010 | Guu et al. | |
| 7,926,401 B2 | 4/2011 | Mishra | |
| 8,002,779 B2 | 8/2011 | Barker et al. | |
| 8,109,187 B2 | 2/2012 | Mishra | |
| 8,162,957 B2 | 4/2012 | Mishra | |
| 8,187,285 B2 | 5/2012 | Eriksson | |
| 8,562,626 B2 | 10/2013 | Sabir | |
| 8,617,181 B2 | 12/2013 | Sabir | |
| 8,926,631 B2 | 1/2015 | Sabir | |
| 9,173,674 B2 | 11/2015 | Sabir et al. | |
| 2001/0029380 A1 | 10/2001 | Ysebaert | |
| 2002/0052614 A1 | 5/2002 | GeBauer | |
| 2002/0092529 A1 | 12/2002 | Rozier | |
| 2003/0009185 A1 | 1/2003 | Jessen | |
| 2003/0069571 A1 | 4/2003 | Treat et al. | |
| 2003/0212357 A1 | 11/2003 | Pace | |
| 2004/0097967 A1 | 5/2004 | Ignon | |
| 2004/0172045 A1 | 9/2004 | Eriksson | |
| 2004/0186498 A1 | 9/2004 | Barnes et al. | |
| 2004/0215217 A1 | 10/2004 | Banbury | |
| 2004/0225309 A1 | 11/2004 | Eriksson | |
| 2004/0230215 A1 | 11/2004 | Eriksson | |
| 2004/0237744 A1 | 12/2004 | Lin | |
| 2005/0038520 A1 | 2/2005 | Binette | |
| 2005/0076921 A1 | 4/2005 | Rozier | |
| 2005/0101972 A1 | 5/2005 | Bhatavadekar | |
| 2005/0221276 A1 | 10/2005 | Rozakis et al. | |
| 2005/0234485 A1 | 10/2005 | Seegert | |
| 2005/0244967 A1 | 11/2005 | Pearlman | |
| 2006/0079852 A1 | 4/2006 | Bubb et al. | |
| 2006/0141616 A1 | 6/2006 | Guu | |
| 2006/0173087 A1 * | 8/2006 | Hyde et al. | 521/82 |
| 2006/0258956 A1 | 11/2006 | Haberstich et al. | |
| 2006/0271070 A1 | 11/2006 | Eriksson | |
| 2006/0287696 A1 | 12/2006 | Wright et al. | |
| 2007/0183974 A1 | 8/2007 | Pearlman | |
| 2007/0255168 A1 | 11/2007 | Hibner et al. | |
| 2008/0146980 A1 | 6/2008 | Rousso | |
| 2009/0085286 A1 | 4/2009 | Grist et al. | |
| 2009/0099122 A1 | 4/2009 | Klinman et al. | |
| 2010/0012311 A1 | 1/2010 | Colongo | |
| 2010/0042127 A1 | 2/2010 | Eriksson | |
| 2010/0121311 A1 | 5/2010 | Seegert et al. | |
| 2010/0145360 A1 | 6/2010 | Eriksson | |
| 2010/0152651 A1 | 6/2010 | Boyden et al. | |
| 2010/0152750 A1 | 6/2010 | Memar | |
| 2010/0286635 A1 | 11/2010 | Watson, Jr. | |
| 2010/0310823 A1 | 12/2010 | Albertelli et al. | |
| 2011/0009882 A1 | 1/2011 | Remsburg et al. | |
| 2011/0077664 A1 | 3/2011 | Schulz | |
| 2011/0251602 A1 | 10/2011 | Anderson | |
| 2011/0264115 A1 | 10/2011 | Asrani et al. | |
| 2011/0282309 A1 * | 11/2011 | Adie | A61M 1/0088 604/319 |
| 2012/0021186 A1 | 1/2012 | Schneider | |
| 2012/0035599 A1 | 2/2012 | Sabir | |
| 2012/0035618 A1 | 2/2012 | Sabir | |
| 2012/0035619 A1 | 2/2012 | Sabir | |
| 2012/0035620 A1 | 2/2012 | Sabir et al. | |
| 2012/0041430 A1 | 2/2012 | Anderson et al. | |
| 2012/0125798 A1 | 5/2012 | Baecker et al. | |

(56) References Cited

U.S. PATENT DOCUMENTS

| | | | |
|---|---|---|---|
| 2012/0136323 A1* | 5/2012 | Stasko et al. | 604/290 |
| 2012/0172894 A1 | 7/2012 | Sabir | |
| 2012/0197267 A1 | 8/2012 | Sabir | |
| 2012/0201755 A1 | 8/2012 | Rozakis et al. | |
| 2012/0201793 A1 | 8/2012 | Bellomo | |
| 2012/0244623 A1 | 9/2012 | Patel | |
| 2012/0271320 A1* | 10/2012 | Hall | A61B 17/32053 606/132 |
| 2013/0041385 A1 | 2/2013 | Giovannoli | |
| 2013/0145596 A1 | 6/2013 | Sabir et al. | |
| 2013/0158627 A1 | 6/2013 | Gozani | |
| 2013/0204273 A1 | 8/2013 | Sabir et al. | |
| 2014/0277454 A1 | 9/2014 | Locke et al. | |
| 2015/0127077 A1 | 5/2015 | Hanan | |
| 2015/0182241 A1 | 7/2015 | Pratt | |

FOREIGN PATENT DOCUMENTS

| | | | |
|---|---|---|---|
| CN | 101053528 A | 10/2007 | |
| EP | 0099748 A1 | 2/1984 | |
| EP | 1092515 A1 | 4/2001 | |
| EP | 1614404 A2 | 1/2006 | |
| EP | 2837370 A1 | 2/2015 | |
| EP | 2837370 A1 * | 2/2015 | A61F 13/02 |
| JP | 2009-095476 A1 | 5/2009 | |
| SU | 772544 A1 | 10/1980 | |
| WO | 1992011879 A1 | 7/1992 | |
| WO | 1995028886 A1 | 11/1995 | |
| WO | 1996018432 A1 | 6/1996 | |
| WO | 1996033768 A2 | 10/1996 | |
| WO | 1997020509 A2 | 6/1997 | |
| WO | 1998016158 A1 | 4/1998 | |
| WO | 2003020333 A2 | 3/2003 | |
| WO | 2003039382 A2 | 5/2003 | |
| WO | 2003049626 A2 | 6/2003 | |
| WO | 2003049783 A2 | 6/2003 | |
| WO | 2003068120 A1 | 8/2003 | |
| WO | 03093418 A2 | 11/2003 | |
| WO | 2004071313 A2 | 8/2004 | |
| WO | 2004075764 A1 | 9/2004 | |
| WO | 2004078032 A2 | 9/2004 | |
| WO | 2004105576 A2 | 12/2004 | |
| WO | 2005033273 A2 | 4/2005 | |
| WO | 2005046428 A2 | 5/2005 | |
| WO | 2007034438 A2 | 3/2007 | |
| WO | 2007117488 A2 | 10/2007 | |
| WO | 2010014716 A1 | 2/2010 | |
| WO | 2010036788 A2 | 4/2010 | |
| WO | 2011038326 A2 | 3/2011 | |
| WO | 2011059441 A1 | 5/2011 | |
| WO | 2011075676 A2 | 6/2011 | |
| WO | 2012019094 A2 | 2/2012 | |
| WO | 2012019095 A2 | 2/2012 | |
| WO | 2012019096 A1 | 2/2012 | |
| WO | 2012019098 A1 | 2/2012 | |
| WO | 2012102812 A1 | 8/2012 | |
| WO | 2012145504 A1 | 10/2012 | |
| WO | 20140152319 A2 | 9/2014 | |

OTHER PUBLICATIONS

PCT Notification of Transmittal of the International Search Report and Written Opinion of the International Searching Authority, or the Declaration, PCT/US2014/027205, dated Oct. 2, 2014 (19 pages.).

Awad, Chinese Cupping: A Simple Method to Obtain Epithelial Grafts for the Management of Resistant Localized Vitiligo, American Society of Dermatologic Surgery, Inc., Dermatol Surg, (2008), 34(9):1186-1193.

Balaji et al., Isolation of a Novel Population of Multipotent Stem Cells From Epidermal Layer of Human Skin, Biology and Medicine, (2010), 2(2):57-67.

Kreis et al., Expansion techniques for skin grafts: comparison between mesh and Meek Island (sandwich-) grafts, Burns, (1994), 20(1):S39-S42.

Lari et al., Expansion technique for skins grafts (Meek technique) in the treatment of severely burned patients, Burns, (2001), 27:61-66.

Meek et al., Successful Microdermagrafting Using the Meek-Wall Microdermatome, Am J Surg, (1958), 96(4):557-558.

Mulekar et al., Treatment of Vitiligo on Difficult-to-Treat Sites Using Autologous Noncultured Cellular Grafting, Dermatol Surg., (2009), 25(1):66-71.

International Search Report and Written Opinion dated Dec. 16, 2011 for International Application No. PCT/US11/46737, 8 pages.

International Search Report and Written Opinion dated Dec. 23, 2011 for International Application No. PCT/US11/46739, 6 pages.

International Search Report and Written Opinion dated Dec. 16, 2011 for International Application No. PCT/US11/46738, 6 pages.

International Search Report and Written Opinion dated Dec. 6, 2011 for International Application No. PCT/US11/46741, 6 pages.

European Examination Report issued Mar. 18, 2015 corresponding to European Application No. 11815368.3 (4 sheets.).

Office Action dated Feb. 20, 2015 with English Text of Office Action corresponding to Japanese Patent Application No. 2013-523359.

International Search Report dated Mar. 11, 2015 for PCT/US2014/072170.

International Search Report dated Mar. 13, 2015 for PCT/US2014/072180.

International Search Report dated Mar. 11, 2015 for PCT/US2014/072188.

Office Action dated Dec. 18, 2014 for U.S. Appl. No. 13/120,799.

Barns et al.. Useful adjuncts to harvest split-thickness skin grafts. Dermatol Surg. Dec. 2004;30(12 Pt 2):1591-2.

Weyandt et al., Split-skin grafting from the scalp: the hidden advantage. Dermatol Surg. Dec. 2009;35(12):1873-9.

International Search Report and Written Opinion dated Feb. 15, 2013 for International Application No. PCT/US2012/068551, 9 pages.

International Search Report and Written Opinion dated Aug. 1, 2014 for International Application No. PCT/US2014/027237, 12 pages.

Extended European Search Report dated Mar. 10, 2016 received in European Application No. 14769345.1, 7 pages.

International Search Report and Written Opinion dated Jun. 28, 2016 for PCT/US2016/026918, 10 pages.

Extended European Search Report received in EP Application No. 17186324.4 dated Nov. 20, 2017; 7 pages.

International Search Report and Written Opinion received in PCT/US2016/060336 dated Feb. 10, 2017; 14 pages.

Invitation to Pay Additional Fees and, Where Applicable, Protest Fee received in PCT/US2017/018431 dated May 26, 2017; 20 pages.

Examination Report received in Australian Application No. 2014239891 dated Nov. 17, 2017; 3 pages.

Office Action dated Jan. 3, 2018 issued in related Chinese Patent Application No. 2016104166749, 6 pages.

* cited by examiner

ABSORBENT SUBSTRATES FOR HARVESTING SKIN GRAFTS

REFERENCE TO RELATED APPLICATIONS

This application claims priority to U.S. Provisional Patent Application No. 61/860,822, filed Jul. 31, 2013 entitled "Absorbent Substrates For Harvesting Skin Grafts", and U.S. Provisional Application No. 61/782,385, filed Mar. 14, 2013, entitled "Absorbent Dressing With Hybrid Drape", the disclosures of which are incorporated by reference in their entirety.

FIELD

The present invention relates generally to medical treatment systems and, more particularly, but not by way of limitation, to absorbent dressings, systems, and methods for harvesting and transplanting skin grafts.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation.

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. As with any surgical procedure, skin grafting involves certain risks. Complications may include graft failure, rejection of the skin graft, bleeding, fluid accumulation or infection at either the donor or recipient site. Additionally, when an autograft is taken from one area of a person's body to produce the graft, some degree of trauma occurs at the donor site. If the recipient site is a large wound or otherwise damaged skin region, the trauma at the donor site can be significant.

Techniques have been developed for harvesting a large number of smaller grafts, e.g., so-called micrografts, to reduce the trauma at the donor site. By removing only a fraction of the skin at a donor site and leaving regions of healthy skin surrounding the excised regions, a large amount of skin for transplantation can be obtained with less discomfort. Micrograft harvesting can also reduce the healing time and risk of infection.

Harvesting of skin grafts can be accomplished in many different ways. One common technique for harvesting a skin graft involves the application of suction to separate a surface portion of the skin, e.g., the epidermis and a basal cell layer, from the underlying dermis. Harvesting of suction blisters typically also involves a heat source to facilitate blister formation.

Various devices are available for generating and harvesting micrografts. For example, the Cellutome™ skin harvester is available from Kinetic Concepts, Inc. of San Antonio, Tex. The Cellutome™ system includes a head that provides a source of reduced pressure (vacuum), and optionally a heater element, and a harvester configured for placement on a target region of a patient's skin. The harvester is further adapted to form a sealing engagement with the head such that the target region of skin is embraced within an evacuated chamber. The Cellutome™ harvester further includes at least one alignment plate having a plurality of holes through which skin blisters can be raised in the presence of negative pressure; and a cutting plate having at least one cutting surface for cleaving skin blisters after they are formed within the chamber.

Typically, micrograft harvesters rely upon a support or substrate to lift the excised blisters from the device. The substrate is then applied to a recipient site so that the plurality of micrografts can be assimilated as transplanted tissue. Ideally, the grafts will expand and coalesce to complete the healing process.

SUMMARY

Methods and devices for management of fluids during skin graft transplantation are disclosed. In one aspect of the invention, absorbent substrates for transplanting skin grafts are disclosed having a surface adapted to contact at least one excised skin graft and engage said graft for removal from a donor site; a sealing member at least partially surrounding an absorbent material disposed within the enclosure; wherein at least a portion of the skin-contacting surface is porous and in fluid communication with the absorbent layer to capture fluids.

In one embodiment of the invention, absorbent substrates for transplanting skin grafts are disclosed including a base layer having a surface adapted to contact at least one excised skin graft and to engage said graft for removal from a donor site; a sealing member peripherally joined to the base layer and defining an enclosure therebetween; and an absorbent material disposed within the enclosure; wherein at least a portion of the base layer is porous and in fluid communication with the absorbent layer to capture fluids.

In certain embodiments the substrate includes a base layer configured for positioning in a chamber of a skin graft harvesting device and, optionally, the base layer is further configured to capture a plurality of skin grafts at the same time.

The base layer of the absorbent substrate preferably includes a biocompatible material, e.g., a material selected from the group of silicones, silicone gels, soft silicones, hydrocolloids, hydrogels, polyurethanes, polyurethane gels, polyolefins, polyolefin gels, hydrogenated styrenic copolymers, hydrogenated styrenic copolymer gels, foamed gels and combinations thereof. In some preferred embodiments, the base layer includes silicone.

In certain embodiments, a skin graft contacting portion of the base layer has an average thickness between about 50 microns and about 10 millimeters, preferably in some cases, between about 500 microns (µm) and about 1000 microns (µm). The skin graft contacting portion of the base layer should also be flexible enough to conform to the shape of the harvester and/or the recipient site. For example, the skin graft contacting portion of the base layer can have a stiffness between about 5 Shore OO and about 80 Shore OO.

In another aspect of the invention, the substrate further includes an adhesive associated with at least a part of the base layer to engage the graft. When used with multi-graft or "micrograft" harvesters, the substrate can further include a pattern of adhesive sites on a skin contacting surface of the base layer, each site arranged and configured to engage a corresponding skin graft raised by a skin graft harvesting device. For example, the substrate can carry a pattern of adhesive sites printed on at least a portion of a skin-contacting surface of the base layer. In certain embodiments, the adhesive can include an acrylic adhesive.

In another aspect of the invention, the base layer can include a plurality of openings to provide passageways from fluid transport from the recipient site to the absorbent material. The openings (e.g., pores) can be spaced apart from each other. In certain embodiments, the openings are generally circular. The openings can have an average cross-sectional dimension ranging from about 0.1 nanometers to about 1 millimeter, or preferably an average cross-sectional dimension ranging from about 1 nanometer to about 100 micrometers. In other embodiments, the pores can be elongated or grid-like and their minor dimension can range from about 0.1 nanometers to about 1 millimeter, or preferably from about 1 nanometer to about 100 micrometers.

In another aspect of the invention, the base layer is patterned to define a plurality of skin graft capture sites and the base layer further includes a network of pores disposed between at least some of the capture sites. Again, the pores (disposed between capture sites) can be circular or elongated and have an average cross-section dimension (or a minor dimension, in the case of elongated pores) ranging from about 0.1 nanometers to about 1 millimeter, or preferably ranging from about 1 nanometers to about 100 micrometers.

In yet another aspect of the invention, the substrate can also include at least one wicking layer disposed in the enclosure and adapted to distribute fluid to the absorbent material. For example, the substrate can include at least a first wicking layer disposed in the enclosure between the base layer and the absorbent material. Alternatively, or in addition to the first wicking layer, the substrate can include one or more additional wicking layers (e.g., a second wicking layer) disposed in the enclosure between the absorbent material and the sealing member. In certain embodiments, the first and/or second wicking layer can have a grain structure adapted to wick fluid along a surface of the wicking layer.

In certain embodiments, the absorbent material is a plurality of absorbent layers, and one or more of the additional absorbent layers are positioned in fluid communication between a first wicking layer and a second wicking layer. The substrate can also include at least one intermediate wicking layer disposed in fluid communication between the absorbent layers. In certain embodiments, a peripheral portion of a first wicking layer can be coupled to a peripheral portion of a second wicking layer to provide a wicking layer enclosure surrounding the absorbent layer between the first and the second wicking layers.

In another aspect of the invention, the absorbent material can include a hydrophilic material that is adapted to absorb fluid and the sealing member is liquid impermeable. For example, the sealing member can include a water-impermeable polyurethane component.

In an alternative embodiment, a unitary absorbent structure can be employed rather than a separate base layer and absorbent material. For example, an absorbent substrate according to this embodiment can include an absorbent material having a surface adapted to contact at least one excised skin graft and engage said graft for removal from a donor site. The absorbent material can further include a sealing member surrounding and defining an enclosure for the absorbent material and substantially sealing the absorbent material except for the skin contacting surface; and wherein at least a portion of skin contacting surface of the absorbent material is porous to capture fluids.

In yet another aspect of the invention, the substrate can further include at least one port for coupling to the reduced pressure source to extract accumulated fluids from the substrate. The port can further include a valve, e.g., a check valve or one-way valve, to prevent backflow of extracted fluids. The port can further include a conduit providing fluid communication between the absorbent material or at least one wicking layer within the chamber and an external fluid receptacle.

In another aspect, the substrate can include at least one removable backing for handling the substrate prior to positioning it in a skin graft harvester. The substrate can further include at least one removable backing for handling the substrate prior to positioning it at a recipient site. For example, the substrate can include at least a first removable backing associated with the base layer for handling the substrate prior to positioning it in a skin graft harvester and a second removable backing for handling the substrate and an associated skin graft prior to positioning it at a recipient site.

In another embodiment, a skin graft transplantation substrate is provided including a base layer, an adhesive, a sealing member, a first wicking layer, a second wicking layer, an absorbent layer, and a conduit interface. The base layer has a periphery surrounding a central portion and a plurality of apertures disposed through the periphery and the central portion, wherein the base layer is adapted to cover the skin graft transplantation site and tissue surrounding the site. The sealing member has a periphery and a central portion, the periphery of the sealing member being positioned proximate the periphery of the base layer such that the central portion of the sealing member and the central portion of the base layer define an enclosure. The first wicking layer and the second wicking layer are each disposed in the enclosure. The absorbent layer is positioned in fluid communication between the first wicking layer and the second wicking layer. A peripheral portion of the first wicking layer is coupled to a peripheral portion of the second wicking layer providing a wicking layer enclosure surrounding the absorbent layer between the first and the second wicking layer. The conduit interface is positioned proximate to the sealing member and in fluid communication with the dressing.

In another aspect, a system is provided for draining a skin transplantation site including a substrate or dressing and a reduced-pressure source. The substrate or dressing is adapted to provide reduced pressure and/or to store fluid extracted from the site. The substrate or dressing includes a base layer, an adhesive, a sealing member, a first wicking layer, a second wicking layer, an absorbent layer, and a conduit interface. The base layer has a periphery surrounding a central portion and a plurality of apertures disposed through the periphery and the central portion. The central portion of the base layer is adapted to be positioned proximate the transplantation site and the periphery of the base layer is adapted to be positioned proximate the tissue surrounding the transplantation site. Further, the periphery of the base layer is adapted to surround the transplantation site, and the apertures in the base layer are adapted to be in fluid communication with site and the tissue surrounding the transplantation site. In certain embodiments, adhesive can be stored or preloaded into apertures in the base layer such that upon placement of the base layer onto the transplantation site, the adhesive is released. (A two-part lower backing can also be employed such that a first (inner) portion of the lower backing is removed when the substrate is joined to a skin graft harvester and a second outer portion of the backing subsequently removed to facilitate peripheral adhesion at the transplantation site.) The sealing member has a periphery and a central portion, the periphery of the sealing member being positioned proximate the periphery of the base layer such that the central portion of the sealing member and the central portion of the base layer define an enclosure. The first wicking layer and the second wicking layer are each disposed in the enclosure. The absorbent layer is positioned in fluid communication between the first wicking layer and the second wicking layer. The conduit interface is positioned proximate to the sealing member and in fluid communication with the dressing. The reduced-pressure source is adapted to be coupled in fluid communication with the conduit interface to provide reduced pressure to the dressing.

In another aspect of the invention, methods are disclosed for fluid management during skin transplantation. The methods can include the steps of contacting at least one skin graft with an absorbent substrate, the substrate comprising a base layer having a surface adapted to contact and engage at least one excised skin graft and a sealing member peripherally joined to the base layer and defining an enclosure therebetween; and an absorbent material disposed within the enclosure; deploying the substrate at a recipient site such that a skin graft that is engaged by the base layer contacts the recipient site; and maintaining the substrate in contact with the recipient site to facilitate transplantation of the graft and removal of fluids.

In another aspect, the methods of the present invention can include maintaining the absorbent substrate at the recipient site, and further, removing excess fluids at the recipient site by extraction into the absorbent material of the substrate. The methods can be practiced by providing a plurality of pores in the base layer to provide a fluid communication path between a recipient site and the absorbent material within the substrate and, optionally, deploying at least one wicking layer within the substrate to distribute fluids captured from a recipient site to different regions of the absorbent material.

In certain embodiments, the methods can further include a step of coupling the substrate to a reduced pressure source to facilitate fluid extraction and, optionally, draining accumulated fluids from the absorbent material into a fluid extraction receptacle or deploying a one-way valve between the absorbent material and the fluid extraction receptacle.

Other aspects, features, and advantages of the illustrative embodiments will become apparent with reference to the drawings and detailed description that follow.

BRIEF DESCRIPTION OF THE DRAWINGS

A more complete understanding of this specification may be obtained by reference to the following detailed description when taken in conjunction with the accompanying drawings wherein.

DETAILED DESCRIPTION

In the following detailed description of non-limiting, illustrative embodiments, reference is made to the accompanying drawings that form a part hereof. Other embodiments may be utilized and logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is not to be taken in a limiting sense, with the scope of the illustrative embodiments being defined by the appended claims.

The term "micrograft" as used herein is intended to encompass skin grafts that have a width or length less than a millimeter, more preferably, less than 100 microns. A micrograft is an excised skin segment having at least one dimension parallel to the skin surface that is less than a millimeter, preferably less than 100 micrometers, more preferably in some applications less than 10 micrometers. The minimum width or length is preferably less than 500 micrometers, preferably less than 100 micrometers or less than 50 micrometers or less than 10 micrometers or less than 1 micrometer. For example, a micrograft can be generally circular, oval or oblong in a plane parallel to the skin surface and have a diameter or major axis that ranges from about 1 millimeter to 0.01 micrometers, or from about 100 micrometers to about 0.1 micrometers, or more preferably from about 50 to 1 micrometers. Micrografts also typically have a depth dimension that extends at least through the epidermis and preferably in some applications encompasses at least one layer of basal cells. The depth can range from about 500 micrometers to about 0.1 micrometers, preferably from about 100 micrometers to about 1 micrometer.

The term "harvesting" as used herein is intended to encompass the removal of one or more skin grafts from an skin graft generating device, such as, for example, a suction blister micrograft generator, as well as the transplantation of such skin grafts and any intermediate steps, such as culturing, expanding, stretching, treating or otherwise preparing a skin graft for transfer to a recipient site.

The terms "generally circular" and "circular" are used interchangeably herein to describe openings that are round, oval or otherwise form closed polygonal shapes having a major dimension (width or diameter) that is less than 5 times the minor dimension (width or diameter) of the shape. Preferably the major dimension is less than 3 times, or less than 2 times, the minor dimension.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Figure 1:
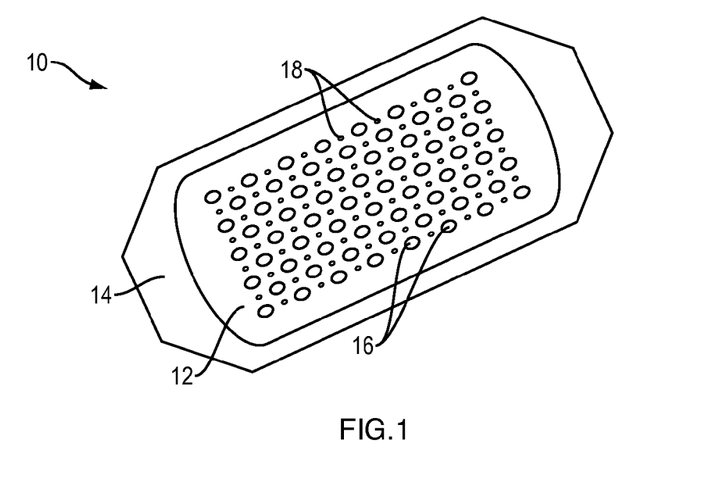
FIG. 1 is a schematic, perspective bottom view of an illustrative embodiment of a absorbent substrate for management of fluids during skin graft transplantation.

Referring to the drawings, FIG. 1 depicts an embodiment of an absorbent substrate 10, viewed from the bottom, showing a base layer 12 and a peripheral removable backing 14. The base layer 12 further includes a plurality of sites 16 for capturing skin grafts. The entire base layer 12 or just the sites 16 can be treated, e.g., coated with an adhesive, to make at least portions of the base layer surface tacky to promote capture of skin grafts. The base layer is also porous and in this illustrated embodiment a plurality of pores 18 are disposed between the graft capture sites 16. The pores 18 can be generally circular or elongated in one or more dimensions. Alternatively, the entire surface of the base layer can be porous or can include a network of lines or cross-shaped incisions or openings. Regardless of the shape or size of the pores 18, the porosity of the base layer 12 should be sufficient to permit fluid migration from a skin segment through the base layer 12 for absorption by the substrate 10.

Figure 2:
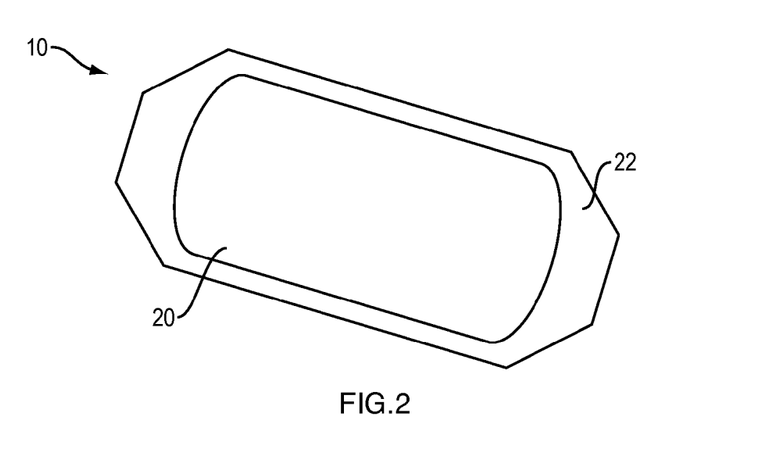
FIG. 2 is a schematic, perspective top view of the absorbent substrate of FIG. 1.
Figure 3:
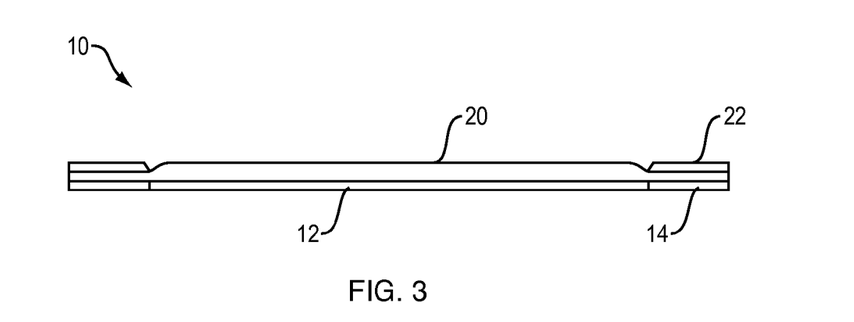
FIG. 3 is a schematic, side view of the absorbent substrate of FIG. 1.

FIG. 2 depicts the absorbent substrate 10 of FIG. 1, viewed from the top, showing a sealing member 20 and a second peripheral removable backing 22 for handling purposes. FIG. 3 is a side view of the same absorbent substrate 10, showing the base layer 12, sealing member 20, and the first (bottom) and second (top) removable backings 14 and 22, respectively.

Figure 4:
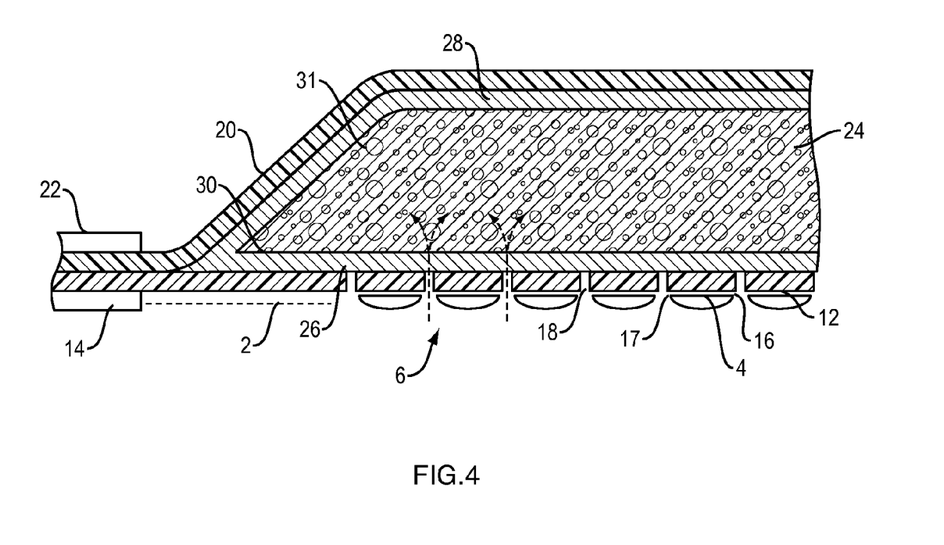
FIG. 4 is a partial cross-sectional view of an absorbent substrate according to the invention.

FIG. 4 is a partial cross-sectional view of an absorbent substrate showing one embodiment of the internal structure. Base layer 12 and sealing member 20 define an enclosure for an absorbent material 24. The figure also schematically shows a plurality of micrografts 4 carried on a bottom surface (e.g., a skin-contacting surface) of the base layer 12. A plurality of pores 18 in the base layer permit fluid ingress and provide passageways to the absorbent material 24. Optionally, one or more wicking layers can be utilized to distribute captured fluids to different portions of the absorbent material. In the illustrated embodiment, a first wicking layer 26 is disposed in proximity to the base layer and a second wicking layer 28 is disposed in proximity to the sealing member 20. Alternatively, wicking material can form alternating layers with absorbent material layers (sandwich style) or wicking material can be distributed throughout or otherwise dispersed within the absorbent material. In the illustrated embodiment, the first and second wicking layers 26, 28, respectively, can be joined together at the periphery to form a seal 30 that completely or substantially encloses the absorbent material.

Additionally, FIG. 4 shows the substrate 10 in use applied to a skin graft transplantation site on a surface of a patient's skin 2 in need of grafting. On the bottom surface of the base layer 12 are a plurality of captured skin grafts 4, which can be placed in contact with the skin 2 as the substrate 10 is applied. Fluid migration from the transplant site and extraction into the absorbent material 24 is illustrated by the dotted lines.

Figure 6:
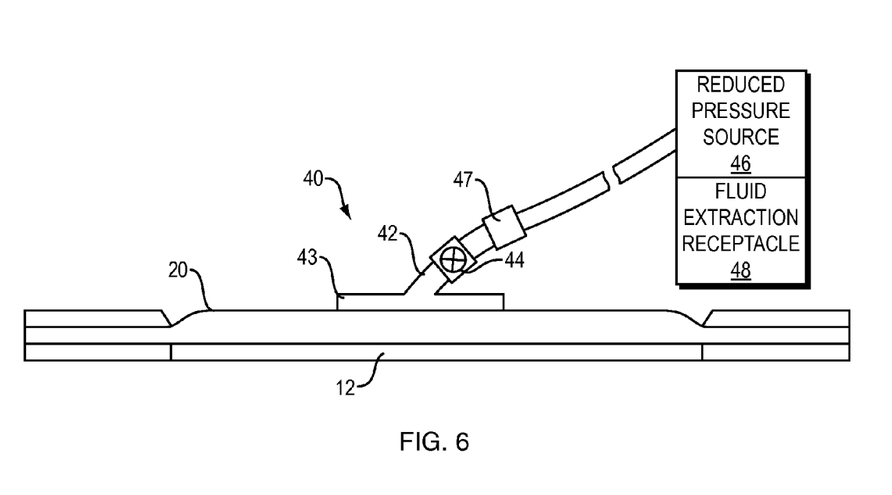
FIG. 6 is a schematic, side view of an alternative embodiment of an absorbent substrate according to the invention having a port for coupling to a reduced pressure source or external fluid drainage receptacle.

FIG. 6 shows another embodiment of an absorbent substrate, having the base layer 12, sealing member 20 and a port 40 for coupling to a source of negative pressure 46 and/or a fluid extraction receptacle 48. The port 40 can further include a conduit 42, one or more filters 47 and/or a check valve 44 to permit fluid extraction (and, optionally, one-way flow) from the absorbent material, e.g., in instances where the absorbent material reaches or nears a saturated state to an external fluid receptacle or a waste disposal site.

Figure 7:
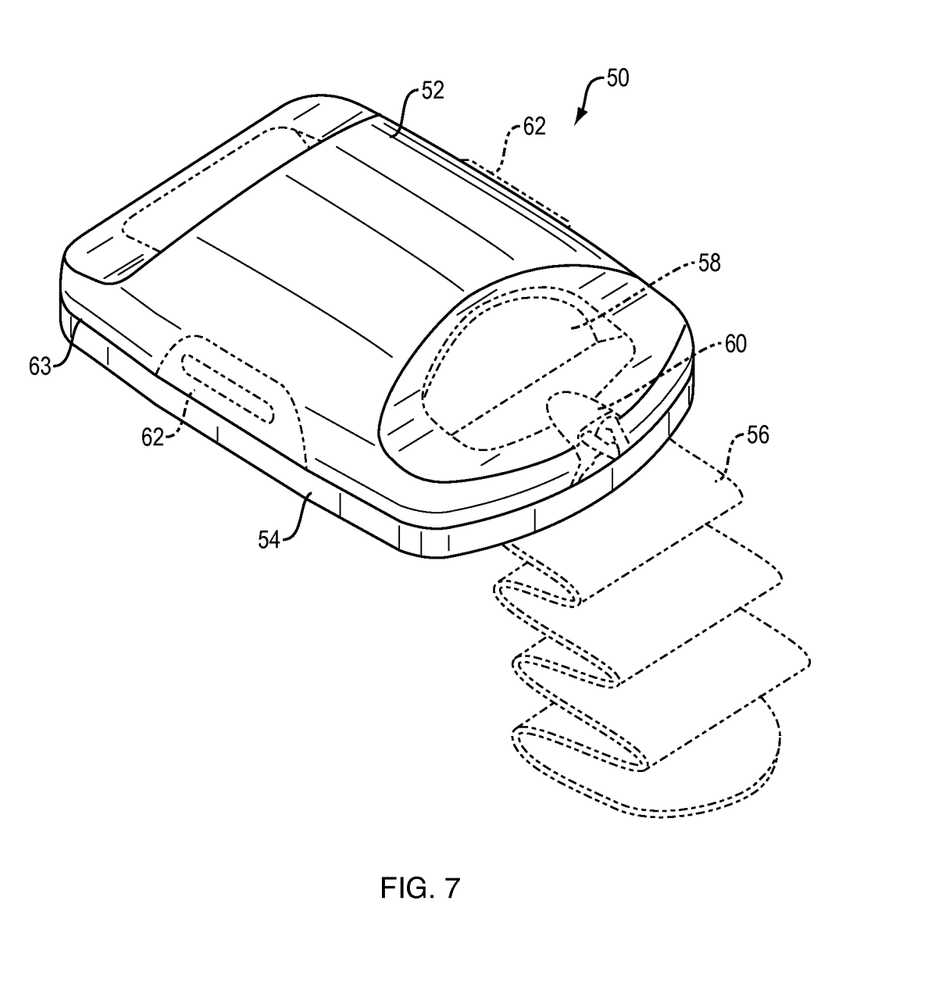
FIG. 7 is a schematic, perspective top view of a skin graft harvester for use with the absorbent substrate.

FIG. 7 is a schematic view of a skin graft harvester 50 for use with an absorbent substrate in accordance with various aspects of the present teachings. In this illustrative embodiment, the harvest 50 includes a detachable head portion 52 and harvester body 54. The harvester body 54 is adapted for placement on a patient's skin at a donor site where skin grafts are to be obtained, e.g., on the inner thigh, and secured in place, for example, with strap 56 (shown in phantom). The head 52 can further include a heater (not shown) powered via a coupler 60 adapted to couple with a power source in a base unit (not shown). The head 52 further includes a seal 63 which permits a reduced pressure chamber to be formed when the head 52 and body 54 are joined together and the harvester 50 is coupled to a vacuum pump or other source of reduced pressure, e.g., via coupler 60 connecting the harvester 50 to its base unit. The head 52 can further include one or more windows 58 for observation of skin blisters being formed within the chamber by application of reduced pressure, heat or both. Once the blisters have been formed, the head 52 can be removed, e.g., by deactivating the source of reduced pressure and by actuation of release levers 62, which break the seal 63 and allow the head 52 to be lifted off the harvester body 54.

Additional details on harvesters useful in connection with the present invention can be found in U.S. patent application Ser. No. 13/839,518 filed Mar. 15, 2013; U.S. patent application Ser. No. 13/346,329 filed Jan. 9, 2012; U.S. patent application Ser. No. 13/436,318 also filed Jan. 9, 2012; U.S. patent application Ser. No. 13/014,737 filed Jan. 27, 2011; U.S. patent application Ser. No. 12/851,656 filed Aug. 6, 2010; U.S. patent application Ser. No. 12/851,621 filed Aug. 6, 2010; U.S. patent application Ser. No. 12/851,703 filed Aug. 6, 2010; and U.S. patent application Ser. No. 12/851,682 filed Aug. 6, 2010. The contents of each of the above-referenced related applications are herein incorporated by reference in their entireties.

Figure 8:
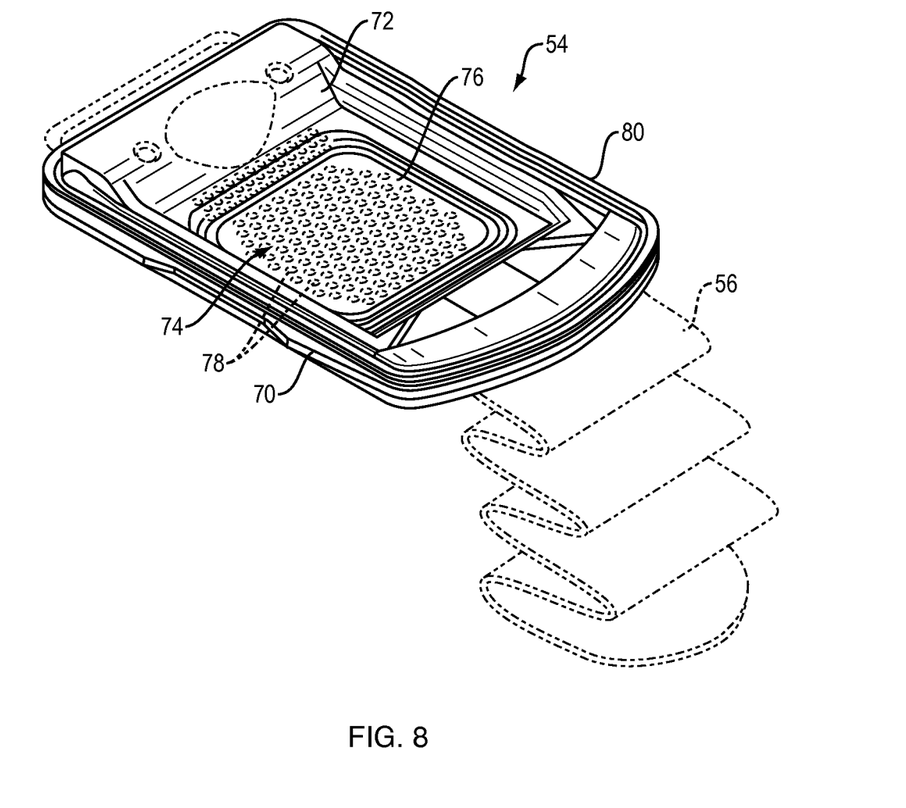
FIG. 8 is a schematic, perspective top view of the skin graft harvester of FIG. 6 with the head component removed and the cutter mechanism exposed.

FIG. 8 is a schematic view of the skin graft harvester 50 of FIG. 7 with the head 52 removed and the cutting mechanism 74 exposed. The harvester body 54 can include a base portion 70, a sled 72, and actuator handle 80. The cutting mechanism 74 can include a plurality of plates with initially aligned holes through which skin blisters are drawn by heat and/or application of suction when the head 52 is joined to the harvester body 54 and activated. Once the blisters are formed, they can be cleaved by the cutting mechanism 74. For example, below the top plate 76 depicted in FIG. 8, one or more additional plates, e.g., a cutter plate and a bottom plate can be deployed with aligned holes. By actuation (e.g., pulling up) of handle 80, the sled 72 is caused to move horizontally such that one of the plates below the top plate 76, e.g., the "cutter plate" (not shown) also moves (because of its linkage to the sled 72), thereby occluding the alignment of holes 78 and cleaving the raised blisters from the donor's skin.

Figure 9:
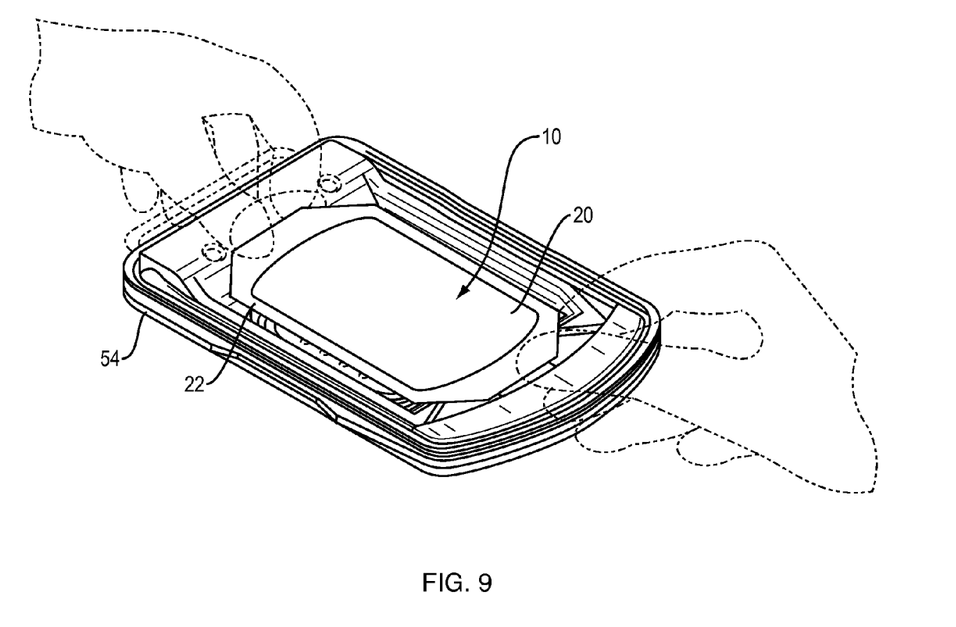
FIG. 9 is a schematic, perspective top view of the skin graft harvester of FIG. 6 with an absorbent substrate according to the invention deployed in the harvester to capture skin grafts.

FIG. 9 is a schematic view of the skin graft harvester 50 of FIG. 7 with an absorbent substrate 10 according to the invention deployed in the harvester body 54 to capture skin grafts. In the illustrated embodiment, the user (e.g., clinician) places the substrate 10 in the harvester holding the backing 22 with the sealing member 20 upwards and the base layer (not visible) in contact with the top plate of cutter mechanism (as shown in FIG. 8). By so placing the substrate, the base layer will also come into contact with the skin blisters. In one preferred embodiment, the substrate is so situated before the cutter mechanism is actuated to cleave the blisters into skin grafts (as described above). In other embodiments, the substrate can be placed onto the harvester after cleavage to capture grafts that have already been cleaved from the skin. In either event the substrate can then be removed from the harvester body 54 and applied to a recipient site, as illustrated in FIG. 4.

Returning to FIGS. 1-4, the base layer 12 may have a periphery surrounding a central portion and a plurality of pores 18 disposed through the periphery and/or the central portion. The pores 18 in the base layer 12 may have any shape, such as, for example, circles, squares, stars, ovals, polygons, slits, complex curves, rectilinear shapes, triangles, or other shapes. The pores 18 may have a uniform pattern or may be randomly distributed on the base layer 12. Each pore 18 has a diameter. In certain embodiments, the average diameter of each of the pores 18 can be between about 6 mm to about 50 mm. The pores 18 may also be sized to enhance the Moisture Vapor Transfer Rate (MVTR) of the dressing 124, described further below.

Alternatively, the base layer can be fluid permeable, e.g., composed of a material that has high water permeability in either liquid or vapor form, such as polyurethanes, polyesters, polyvinyl chlorides, copolymers of vinyl chloride and vinyl acetate or vinyl chloride and ethylene, polyolefins, polyamides, polyethylene, polypropylene, silicone or polystyrenes, polyacrylics, polyacrylates, polyvinyl alcohol, and copolymers thereof. Examples of water permeable materials include polyurethane films, such as Ensure-IT dressing (Deseret Medical, Inc.) and POLYSKIN® transparent dressing (Kendall Company, Boston, Mass.).

Various techniques can be employed to increase the permeability or porosity of polymer films, such as the incorporation of inclusions during polymer processing that are subsequently dissolved or evaporated away to leave micro-sized or nano-sized voids, e.g., voids having an average width ranging from about 0.1 nanometers to about 1 millimeter or from about 1 nanometer to about 100 micrometers. In certain embodiments, micro-pores having an average width of about 0.1 micrometers to about 1 millimeter can be desired. In other embodiments, nano-pores having an average size of about 0.1 to about 100 nanometers, preferably about 1 to about 100 nanometers or about 1 to about 10 nanometers, can be advantageous.

In another embodiment, a permeable or porous base layer can be formed from woven or non-woven (e.g., matted) fibers. The fibrous base layer can include microfibers and/or nanofibers. In certain embodiments, microfibers having an average diameter of about 0.1 to about 10 micrometers can be desired. In other embodiments, nanofibers having an average diameter of about 1 to about 100 nanometers, preferably about 20 to about 80 nanometers, although in some instances, fibers with diameters about 1 to about 20 nanometers, can also be advantageous.

In yet another embodiment, the base layer can be a foamed material, such as an open cell polymer foam that is formed through the use of chemical and/or physical blowing agents during polymer processing. The foamed base layer should have a sufficiently open cell structure such that fluid passageways are formed through the full thickness of the foamed base layer to facilitate fluid extraction. The average width of the open cells can range from about 1 nanometer to about 1 millimeter, preferably in some instances from about 10 nanometer to about 100 micrometers, or from about 100 nanometers to 10 micrometers. Foam polymers can have from about 1 to 1000 pores per square inch, preferably in some instances, from about 10 to 100 pores per square inch. Preferred foam polymers can void fractions from about 10 to about 90 percent, or void fractions greater than 20 percent, 30 percent, 40 percent or 50 percent.

The terms "porous" as used herein is intended to encompass not only apertures or holes but also permeable and open cell foam structures as described above.

The base layer 12, in certain embodiments, is preferably a soft material suitable for providing a fluid seal with the skin graft transplantation site as described herein. For example, the base layer 12 may comprise a silicone gel, a soft silicone, hydrocolloid, hydrogel, polyurethane gel, polyolefin gel, hydrogenated styrenic copolymer gels, a foamed gel, a soft closed cell foam such as polyurethanes and polyolefins, polyurethane, polyolefin, or hydrogenated styrenic copolymers coated with an adhesive described below. The base layer 12 can have a thickness between about 500 microns (µm) and about 1000 microns (µm). In one embodiment, the base layer 12 has a stiffness between about 5 Shore OO and about 80 Shore OO. The base layer 12 can include hydrophobic or hydrophilic materials.

In some embodiments, the base layer 12 may be a hydrophobic-coated material. For example, the base layer 12 may be formed by coating a mesh or porous material, such as, for example, woven, nonwoven, molded, or extruded mesh with a hydrophobic material. The hydrophobic material for the coating may be a soft silicone, for example.

The adhesive 17 used to capture skin grafts and/or adhere the substrate 10 to a patient at the transplantation site may be any medically-acceptable adhesive. For example, the adhesive 17 may comprise an acrylic adhesive, rubber adhesive, high-tack silicone adhesive, polyurethane, or other adhesive substance. In some embodiments, the adhesive 17 may be a pressure-sensitive adhesive comprising an acrylic adhesive with a coating weight of 15 grams/$m^2$ (gsm) to 70 grams/$m^2$ (gsm). The adhesive 17 may be a continuous or a discontinuous layer of material. Discontinuities in the adhesive 17 may be provided by pores 18 in the base layer 12. The apertures in the adhesive may be formed after application of the adhesive to the base layer or by coating the adhesive 17 in patterns on the base layer.

Factors that may be utilized to control the adhesion strength of the substrate 10 may include the diameter and number of the pores 18 in the base layer 12, the thickness of the base layer 12, the thickness and amount of the adhesive 17, and the tackiness of the adhesive 17. An increase in the amount of the adhesive 17 generally corresponds to an increase in the adhesion strength of the substrate 10. Thus, the size and configuration of the adhesive coated portions of the base layer 12, the thickness of the base layer 12, and the amount and tackiness of the adhesive utilized may be varied to provide a desired adhesion strength for the substrate 10. For example, the thickness of the base layer 12 may be about 200 microns, and the adhesive layer 17 may have a thickness of about 30 microns and a tackiness of 2000 grams per 25 centimeter wide strip.

Continuing with FIGS. 1-4, the sealing member 20 has a periphery and a central portion. The periphery of the sealing member 20 may be positioned proximate the periphery of the base layer 12 such that the central portion of the sealing member 20 and the central portion of the base layer 12 define an enclosure.

The sealing member 20 may cover the tissue site 6 to provide a fluid seal and a sealed space between the tissue site 6 and the sealing member 20 of the substrate 10. Further, the sealing member 20 may cover tissue, such as a portion of the epidermis 106, surrounding the tissue site 6 to provide the fluid seal.

The sealing member 20 may be formed from any material that allows for a fluid seal. A fluid seal is a seal adequate to maintain reduced pressure at a desired site given the particular reduced pressure source or system involved. The sealing member 20 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material.

The sealing member 20 may allow vapor to exit while inhibiting liquids from exiting the sealed space provided by the substrate 10. The sealing member 20 may be a flexible, breathable film having a high MVTR of, for example, at least about 300 g/m$^2$ per 24 hours. The sealing member 20 may comprise a range of medically suitable films having a thickness between about 15 microns (μm) to about 50 microns (μm). In other embodiments, a low or no vapor transfer drape can be used as the sealing member.

The fluid management assembly may be disposed in the enclosure 31 and may include a first wicking layer 26, a second wicking layer 28, and an absorbent layer 24. The absorbent layer 24 may be positioned in fluid communication between the first wicking layer 26 and the second wicking layer 28. The first wicking layer 26 may have a grain structure (not shown) adapted to wick fluid along a surface of the first wicking layer 26. Similarly, the second wicking layer 28 may have a grain structure (not shown) adapted to wick fluid along a surface of the second wicking layer 28. For example, the first and the second wicking layer 26, 28 may wick or otherwise transport fluid in a lateral direction along the surfaces of the first and the second wicking layer 26, 28, respectively. The surfaces of the first and the second wicking layer 26, 28 may be normal relative to the thickness of each of the first and the second wicking layer 26, 28. The wicking of fluid along the first and the second wicking layers 26, 28 may enhance the distribution of the fluid over a surface area of the absorbent layer 24 that may increase absorbent efficiency and resist fluid blockages. Fluid blockages may be caused, for example, by fluid pooling in particular location in the absorbent layer 24 rather than being distributed more uniformly across the absorbent layer 24. The laminate combination of the first and the second wicking layer 26, 28 and the absorbent layer 24 may be adapted as described above to maintain an open structure, resistant to blockage, that can maintain fluid communication with, for example, the tissue site 6.

The substrate 10 may include, without limitation, any number of wicking layers and absorbent layers as desired for treating a particular tissue site. For example, the absorbent layer 24 may be a plurality of absorbent layers 24 positioned in fluid communication between the first wicking layer 26 and the second wicking layer 28 as described above. Further, at least one intermediate wicking layer may be disposed in fluid communication between the plurality of absorbent layers 24. Similar to the absorbent layer 24 described above, the plurality of absorbent layers 24 and the at least one intermediate wicking layer may be positioned within the wicking layer enclosure.

In one embodiment, the absorbent material or layer 24 may be a hydrophilic material adapted to absorb fluid from, for example, the tissue site 6. Materials suitable for the absorbent layer 184 may include Luquafleece® material, Texus FP2326, BASF 402c, Technical Absorbents 2317 available from Technical Absorbents (www.techabsorbents.com), sodium polyacrylate super absorbers, cellulosics (carboxy methyl cellulose and salts such as sodium CMC), or alginates. Materials suitable for the first and second wicking layers 26, 28 may include any material having a grain structure capable of wicking fluid as described herein, such as, for example, Libeltex TDL2 80 gsm.

The substrate 10 can be a pre-laminated structure manufactured at a single location or simply individual layers of material stacked upon one another as described above. Individual layers of the substrate 10 may be bonded or otherwise secured to one another without adversely affecting fluid management by, for example, utilizing a solvent or non-solvent adhesive, or by thermal welding.

In one embodiment, the enclosure 31 defined by the base layer 12 and the sealing member 20 may include an anti-microbial layer. The addition of the anti-microbial agent may reduce the probability of excessive bacterial growth within the dressing 10 to permit the dressing 10 to remain in place for an extended period. The anti-microbial material may be, for example, an additional layer included as a part of the substrate 10 as depicted in FIGS. 1-4, or a coating of an anti-microbial agent disposed in any suitable location within the substrate 10. The anti-microbial material may include elemental silver or similar compounds, for example.

Figure 5A:
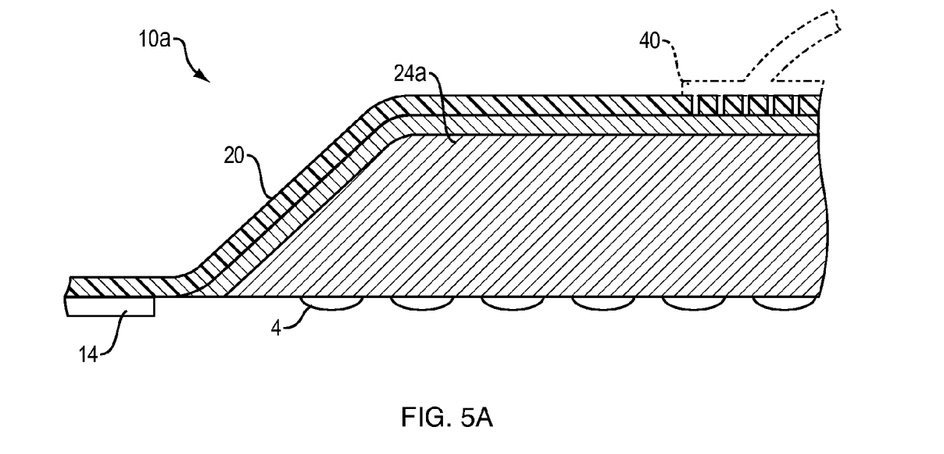
FIG. 5A is partial cross-sectional view of another absorbent substrate according to the invention in which the baser layer and absorbent material are a unitary structure.
Figure 5B:
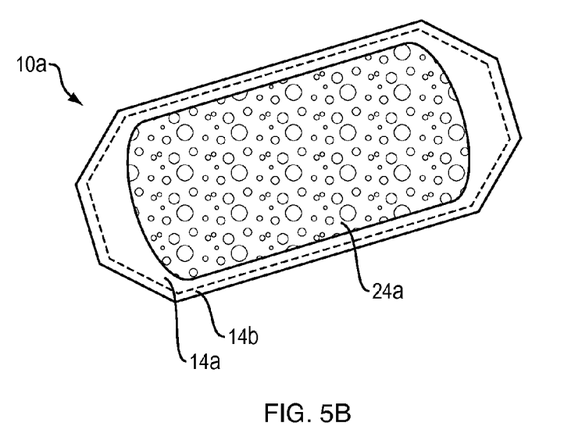
FIG. 5B is schematic perspective bottom view of the substrate of FIG. 5A.

In an alternative embodiment, the base layer and absorbent material can be replaced by a single, unitary element (with or without wicking material) that provides both the skin-contacting and the fluid absorbing functions. FIGS. 5A and 5B illustrates such a substrate 10A including absorbent base 24A, an optional upper wicking layer and a sealing member 20. The substrate can further include a peripheral portion that does not have a foamed or sponge surface for securing the substrate to a patient's skin and/or a harvester for collection of skin grafts. As discussed above a backing can be disposed over this peripheral portion for handling purposes. The absorbent base can be a foamed polymer (e.g., a sponge) capable of attracting and absorbing fluids when placed in contact with the skin and optionally can further include a port 40 (shown in phantom) for coupling to a source of a source of reduced pressure as discussed above.

In this context the absorbent material having a skin-contacting surface in lieu of a separate base layer can be a sponge material, e.g., an elastic open pore structured polymer such as cellulose, collagen, gelatin/alginate, polyesters, polyethers, polyvinyl acetates, polyvinyl acetals, polyurethanes, gelatin/hyaluronates or chitosan/hyaluronates, polyvinyl alcohol, and polyacrylates. The sponge material can have a network of interconnected pores for fluid transport, the average cross-sectional width of which can range from 0.05 millimeters (mm) to about 5 millimeters (mm), more preferably from about 0.1 mm to about 1 mm in certain embodiments.

FIG. 5B also shows another feature of the invention that can be used in any of the illustrated embodiments, namely a split lower backing. An inner portion of the backing 14A can be removed when the substrate is applied to the harvester to capture skin grafts. The surface beneath the backing 14A can include an adhesive for coupling to the harvester and a second portion of the backing 14B can remain in place until transplantation, at which time it can be removed exposing another portion of the surface (and optionally an adhesive) for contact with the skin. The function (or position) of backings 14A and 14B can, of course, be reversed. Various other arrangements can likewise be employed to permit securement of the substrate both at the time of harvesting and at transplantation.

Referring now to FIG. 6, the port 40 for coupling to a source of reduced pressure can be positioned proximate to the sealing member 20 and in fluid communication with the absorbent material 24 through an aperture (not shown) in the sealing member 20 to provide reduced pressure from the reduced-pressure source 46 to the substrate 10. The port 40 may comprise a medical-grade, soft polymer or other pliable material. As non-limiting examples, the port 40 may be formed from polyurethane, polyethylene, polyvinyl chloride (PVC), fluorosilicone, or ethylene-propylene, etc. In one illustrative, non-limiting embodiment, port 40 may be molded from DEHP-free PVC. The port 40 may be formed in any suitable manner such as by molding, casting, machining, or extruding. Further, the port 40 may be formed as an integral unit or as individual components and may be coupled to the substrate 10 by, for example, adhesive, welding or mechanical coupling.

The port 40 can also include one or more filters 47, e.g., an odor filter to inhibit the passage of odors from the tissue site 6 out of the sealed substrate 10, or a hydrophobic filter. The filter 47 can be disposed in the conduit 42 or other suitable location such that fluid communication between the reduced-pressure source 46 and the substrate is provided through the filter 47. In another embodiment, the filters 47 can be positioned in any exit location in the substrate 10, such as an aperture (not shown), that is in fluid communication with the atmosphere or with the reduced-pressure source 46. The filter 47 may also be positioned in any suitable location in the substrate that is in fluid communication with the graft transplantation site 6.

For example, an odor filter 47 may include a carbon material in the form of a layer or particulate, such as a woven carbon cloth filter such as those manufactured by Chemviron Carbon, Ltd. of Lancashire, United Kingdom (www.chemvironcarbon.com). A hydrophobic filter 47 may be comprised of a material that is liquid impermeable and vapor permeable, such as a material manufactured under the designation MMT-314 by W.L. Gore & Associates, Inc. of Newark, Del., United States, or similar materials.

Continuing with FIG. 6, the reduced-pressure source 46 provides reduced pressure to the substrate 10 and the sealed space 31. The reduced-pressure source 46 may be any suitable device for providing reduced pressure as described herein, such as, for example, a vacuum pump, wall suction, or other source. Additional details on reduced pressure sources can be found, for example, in U.S. patent application Ser. No. 11/646,918 filed Dec. 28, 2006, U.S. patent application Ser. No. 11/810,027 filed Jun. 4, 2007; U.S. patent application Ser. No. 12/661,293 filed Mar. 15, 2010; and U.S. patent application Ser. No. 13/052,873 filed Mar. 21, 2011. The disclosures of each of these patent applications are incorporated by reference in their entireties.

As used herein, "reduced pressure" generally refers to a pressure less than the ambient pressure at a tissue site being subjected to treatment. Typically, this reduced pressure will be less than the atmospheric pressure. The reduced pressure may also be less than a hydrostatic pressure at a tissue site. Unless otherwise indicated, values of pressure stated herein are gauge pressures. While the amount and nature of reduced pressure applied to a tissue site will typically vary according to the application, the reduced pressure will typically be between −5 mmHg and −500 mmHg, and more typically in a therapeutic range between −100 mmHg and −200 mmHg.

The reduced pressure delivered may be constant or varied (e.g., patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. An increase in reduced pressure corresponds to a reduction in pressure (more negative relative to ambient pressure) and a decrease in reduced pressure corresponds to an increase in pressure (less negative relative to ambient pressure).

A conduit 42 having an internal lumen may be coupled in fluid communication between the reduced-pressure source 46 and the substrate 10. The conduit interface 43 may be coupled in fluid communication with the dressing and adapted to connect between the conduit 42 and the substrate 10 for providing fluid communication with the reduced-pressure source 46. The conduit interface 43 may be fluidly coupled to the conduit 42 in any suitable manner, such as, for example, by an adhesive, solvent or non-solvent bonding, welding, or interference fit. An aperture (not shown) in the sealing member 20 may provide fluid communication between the substrate and the conduit interface 43. In one embodiment, the conduit 42 may be inserted into the substrate 10 through an aperture (not shown) in the sealing member 20 to provide fluid communication with the reduced-pressure source 46 without utilization of the conduit interface 43. The reduced-pressure source 46 may also be directly coupled in fluid communication with the substrate 10 and/or the sealing member 20. The conduit 42 may be, for example, a flexible polymer tube. A distal end of the conduit 42 may include any one of known couplings for attachment to the reduced-pressure source 46.

Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

The invention claimed is:

1. An absorbent substrate for transplanting a skin graft, comprising:
   a base layer having a plurality of pores and having at least one adhesive site adapted to contact at least one excised skin graft and capture said graft for removal from a donor site;
   a sealing member peripherally joined to the base layer and defining an enclosure therebetween;

an absorbent material disposed within the enclosure; and
at least a first wicking layer and a second wicking layer disposed in the enclosure between the base layer and the absorbent material, said first wicking layer having a grain structure adapted to transport fluid in a lateral direction along a surface thereof, the second wicking layer being disposed adjacent to the sealing member and the first and second wicking layers being joined together to form a seal that encloses the absorbent material;
wherein at least a portion of the base layer is in fluid communication with the absorbent material to capture fluids.

2. The substrate of claim 1, wherein the base layer is configured to be positioned in a chamber of a skin graft harvesting device.

3. The substrate of claim 2, wherein the base layer is configured to capture a plurality of skin grafts at the same time.

4. The substrate of claim 1, wherein the base layer comprises a biocompatible material.

5. The substrate of claim 4, wherein the biocompatible material, is selected from the group of silicones, silicone gels, soft silicones, hydrocolloids, hydrogels, polyurethanes, polyurethane gels, polyolefins, polyolefin gels, hydrogenated styrenic copolymers, hydrogenated styrenic copolymer gels, foamed gels and combinations thereof.

6. The substrate of claim 1, wherein the base layer comprises a silicone.

7. The substrate of claim 1, wherein the skin graft contacting portion of the base layer has an average thickness between about 500 microns (μm) and about 1000 microns (μm).

8. The substrate of claim 1, wherein the skin graft contacting portion of the base layer has a stiffness between about 5 Shore OO and about 80 Shore OO.

9. The substrate of claim 1, wherein the at least one adhesive site comprises a coating of an adhesive material on at least a portion of the base layer.

10. The substrate of claim 9, wherein the adhesive material comprises an acrylic adhesive.

11. The substrate of claim 1, wherein the at least one adhesive site comprises a pattern of adhesive sites.

12. The substrate of claim 1, wherein the at least one adhesive site comprises a plurality of adhesive sites printed on at least a portion of a skin-contacting surface of the base layer.

13. The substrate of claim 1, wherein the plurality of pores provides passageways for fluid transport from the recipient site to the absorbent material.

14. The substrate of claim 13, wherein the base layer comprises a foamed polymer.

15. The substrate of claim 13, wherein the base layer comprises a fluid permeable polymeric material.

16. The substrate of claim 13, wherein the base layer comprises a fibrous material.

17. The substrate of claim 16, wherein the fibrous material comprises a plurality of microfibers having an average diameter of about 0.1 micrometers to about 10 micrometers.

18. The substrate of claim 16, wherein the fibrous material comprises a plurality of nanofibers having an average diameter of about 1 nanometer to about 100 nanometers.

19. The substrate of claim 16, wherein the fibrous material comprises a plurality of nanofibers having an average diameter of about 20 nanometers to about 80 nanometers.

20. The substrate of claim 13, wherein the pores have an average cross-sectional dimension ranging from about 1 nanometer to about 1 millimeter.

21. The substrate of claim 13, wherein the pores have an average cross-sectional dimension ranging from about 1 nanometer to about 100 micrometers.

22. The substrate of claim 1, wherein the at least one adhesive site comprise a plurality of adhesive sites defining a plurality of skin graft capture sites and wherein the base layer further comprises a network of pores disposed between at least some of the capture sites.

23. The substrate of claim 22, wherein the pores are generally circular and have an average cross-sectional dimension ranging from about 1 nanometer to about 1 millimeter.

24. The substrate of claim 23, wherein the pores have an average cross-sectional dimension ranging from about 1 nanometer to about 100 micrometers.

25. The substrate of claim 1, wherein the substrate further comprises at least one wicking layer disposed in the enclosure and adapted to distribute fluid to the absorbent material.

26. The substrate of claim 1, wherein the second wicking layer has a grain structure adapted to wick fluid in a lateral direction along a surface of the second wicking layer.

27. The substrate of claim 26, wherein the absorbent material comprises a plurality of absorbent layers, and wherein the plurality of absorbent layers are positioned in fluid communication between the first wicking layer and the second wicking layer.

28. The substrate of claim 27, further comprising at least one intermediate wicking layer disposed in fluid communication between the absorbent layers.

29. The substrate of claim 1, wherein a peripheral portion of the first wicking layer is coupled to a peripheral portion of the second wicking layer providing a wicking layer enclosure surrounding the absorbent material between the first and the second wicking layer.

30. The substrate of claim 1, wherein the absorbent material comprises a hydrophilic material that is adapted to absorb fluid.

31. The substrate of claim 1, wherein the sealing member is liquid impermeable.

32. The substrate of claim 1, wherein the sealing member comprises polyurethane.

33. The substrate of claim 1, further comprising a port for coupling to a reduced pressure source to extract accumulated fluids from the substrate.

34. The substrate of claim 33, wherein the port further comprises a valve.

35. The substrate of claim 33, wherein the port further comprises a conduit providing fluid communication between the absorbent material or at least one wicking layer within the enclosure and an external fluid receptacle.

36. The substrate of claim 1, wherein the substrate comprises at least one removable backing for handling the substrate prior to positioning in a skin graft harvester.

37. The substrate of claim 1, wherein the substrate comprises at least one removable backing for handling the substrate prior to positioning at a recipient site.

38. The substrate of claim 1, wherein the substrate comprises at least a first removable backing associated with the base layer for handling the substrate prior to positioning in a skin graft harvester and a second removable backing for handling the substrate and an associated skin graft prior to positioning at a recipient site.

39. The substrate of claim 1, wherein the base layer and the absorbent material are formed as a unitary structure.

40. An absorbent substrate for transplanting a skin graft, comprising:

a base layer having a plurality of pores and having at least one adhesive site adapted to contact at least one excised skin graft and capture said graft for removal from a donor site, said pores having an average width in a range of about 1 nanometer to about 10 micrometers;

a sealing member peripherally joined to the base layer and defining an enclosure therebetween;

an absorbent material disposed within the enclosure; and at least a first wicking layer and a second wicking layer disposed in the enclosure between the base layer and the absorbent material, the second wicking layer being disposed adjacent to the sealing member and the first and second wicking layers being joined together to form a seal that encloses the absorbent material;

wherein at least a portion of the base layer is in fluid communication with the absorbent material to capture fluids.

41. The substrate of claim 40, wherein said base layer comprises a biocompatible material.

42. The substrate of claim 41, wherein said biocompatible material is selected from the group of silicones, silicone gels, soft silicones, hydrocolloids, hydrogels, polyurethanes, polyurethane gels, polyolefins, polyolefin gels, hydrogenated styrenic copolymers, hydrogenated styrenic copolymer gels, foamed gels and combinations thereof.

43. The substrate of claim 40, wherein the skin graft contacting portion of the base layer has an average thickness between about 500 microns and about 1000 microns.

44. The substrate of claim 40, wherein the skin graft contacting portion of the base layer has a stiffness between about 5 Shore OO and about 80 Shore OO.

* * * * *